US 9,974,506 B2

(12) United States Patent
Beymer et al.

(10) Patent No.: US 9,974,506 B2
(45) Date of Patent: May 22, 2018

(54) ASSOCIATING CORONARY ANGIOGRAPHY IMAGE ANNOTATIONS WITH SYNTAX SCORES FOR ASSESSMENT OF CORONARY ARTERY DISEASE

(71) Applicant: International Business Machines Corporation, Armonk, NY (US)

(72) Inventors: David J. Beymer, San Jose, CA (US); Tanveer F. Syeda-Mahmood, Cupertino, CA (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 903 days.

(21) Appl. No.: 14/071,842

(22) Filed: Nov. 5, 2013

(65) Prior Publication Data

US 2015/0126860 A1 May 7, 2015

(51) Int. Cl.
*A61B 6/00* (2006.01)
*G06F 19/00* (2018.01)

(52) U.S. Cl.
CPC .............. *A61B 6/468* (2013.01); *A61B 6/504* (2013.01); *G06F 19/321* (2013.01); *G06F 19/3431* (2013.01); *G06F 19/363* (2013.01); *A61B 6/481* (2013.01)

(58) Field of Classification Search
CPC ................................ A61B 6/481; A61B 6/504
See application file for complete search history.

(56) References Cited

U.S. PATENT DOCUMENTS

| 7,162,063 B1 * | 1/2007 | Craine .................. G06T 7/0012 128/922 |
| 7,583,827 B2 | 9/2009 | Hansen et al. |
| 7,593,559 B2 | 9/2009 | Toth et al. |

(Continued)

OTHER PUBLICATIONS

Beymer et al., "AALIM AngioViewer: A tool for SYNTAX score computation and assessing the state of coronary arter disease", 2011 IBM Corporation, Healthcare Informatics, IBM Almaden Research Center, Feb. 2011, 2 pgs.

(Continued)

*Primary Examiner* — Hien Nguyen
(74) *Attorney, Agent, or Firm* — Cantor Colburn LLP (57) ABSTRACT

Embodiments relate to associating coronary angiography image annotations with SYNTAX score for assessment of coronary artery disease. Aspects include receiving and processing a plurality of angiogram videos from a coronary angiography study into a plurality of frames, selecting and displaying a key frame from the plurality of frames for each angiogram video in a browsing interface, and receiving a selection of one of the key frame from a user. Aspects further include displaying the angiogram video associated with the selected key frame in a video viewer interface, receiving a lesion annotation from the user for a frame of the angiogram video, and displaying a SYNTAX score questionnaire in the video viewer interface. Aspects further include annotating the frame of the angiogram video with the answers to the SYNTAX score questionnaire from the user and saving the answers to the SYNTAX score questionnaire with the annotated frame in a database.

14 Claims, 6 Drawing Sheets

(56) References Cited

U.S. PATENT DOCUMENTS

| | | | |
|---|---|---|---|
| 2009/0187106 A1* | 7/2009 | Lee | A61B 8/481 600/458 |
| 2012/0078099 A1* | 3/2012 | Suri | A61B 8/483 600/440 |
| 2012/0177275 A1 | 7/2012 | Suri | |
| 2012/0243764 A1* | 9/2012 | Dey | A61B 6/032 382/131 |
| 2013/0210040 A1* | 8/2013 | Sargent | G01N 33/689 435/7.93 |
| 2014/0114618 A1* | 4/2014 | Fonte | G06T 19/00 703/1 |

OTHER PUBLICATIONS

Siemens AG and Carstens, J., "Automatic Linkage and Synchronized Annotation in Radiology Reports and Patient Images", an IP.com Prior Art Database Technical Disclosure; Published Mar. 27, 2009, IP.com No. IPCOM000180632D; IP.com; Electronic Publication: Mar. 13, 2009, 2 pgs.

* cited by examiner

ASSOCIATING CORONARY ANGIOGRAPHY IMAGE ANNOTATIONS WITH SYNTAX SCORES FOR ASSESSMENT OF CORONARY ARTERY DISEASE

BACKGROUND

Embodiments of the invention relate generally to angiogram analysis, and more specifically, to associating coronary angiography image annotations with SYNTAX scores for assessment of coronary artery disease.

Cardiovascular disease (CVD) results in more death and disability in both males and females in all western societies than any other disease category, accounting for one third of all deaths in the United States in 2007. Half of these deaths are due to coronary artery disease (CAD), which is the process of atherosclerotic narrowing of coronary arteries which are arteries that supply blood and oxygen to the heart muscle. Any occlusion of these arteries can impact heart function leading to effort intolerance with exertion provoked chest symptoms, heart attack, permanent impairment of heart muscle function, and sudden death.

The "gold standard" diagnostic test for CAD is the coronary angiogram. A coronary angiogram involves placing plastic catheters into the arterial system and injecting iodinated contrast solution into the coronary blood flow, to obtain a silhouette of the coronary arterial wall. The angiographic images are typically recorded at 15 or 30 frames a second, providing a motion picture of the flowing blood and contrast mixture to permit the identification of segmental coronary narrowing or blockage attributable to atherosclerotic plaque accumulation along the interior wall of the artery.

Interpretation of coronary angiograms is nearly always performed by visual estimation of the severity of narrowing in the diseased coronary artery, stated in percent of diameter lost in projections that display the narrowing at its worst. Because of the curvilinear cylindrical structure of an artery and the irregular and often eccentric remaining lumen through the diseased segment, several viewpoints are inspected in the effort to estimate the percentage of narrowing.

Abnormal coronary angiographic findings can be treated by medications, or one of two "revascularization" methods to improve blood flow, coronary artery bypass grafting (CABG) or open heart surgery, and percutaneous coronary interventions (PCI) of balloon angioplasty with coronary stent placement. The former is performed by cardiothoracic surgeons in an operating room under general anesthesia, while PCI is performed in the catheter lab often immediately following coronary angiography, and the patient is discharged home within 24 hours and fully active after three days. There are thus major differences in the cost and impact to patients so that decision making between these options cannot be taken lightly and will depend on the accurate assessment of the state of the coronary artery disease.

A scoring system called the SYNTAX score was developed by cardiologists to quantify the severity and extent of CAD and to reduce observer bias in the interpretation of the angiographic findings and assure equal severity of disease in both treatment groups. The score is calculated in response to 12 questions asking a specialist to describe the coronary artery system they see in a coronary angiogram, including questions about coronary dominance, number of lesions, locations of vessels involved, tortuosity, diffuse arteries, etc. The calculation of the SYNTAX score, however, is a time consuming and dependent on operator training and remains subject to visual quantification biases. Currently, the available methods of calculating the SYNTAX score is either through a paper questionnaire or through an online site syntaxscore.com where the questions are interactively displayed. To answer these questions, the coronary angiogram must be loaded from a picture archiving and communication system (PACS) and be simultaneously visible. There is currently no way to associate the imaging data directly with the questionnaire in order to indicate the lesions based on which the questionnaire was answered. As a result of these difficulties, the SYNTAX score, though often mentioned in discussion of treatment decisions, is rarely actually calculated in the process of routine clinical care. Ideally, a fully automated, operator independent and bias free program would quickly generate a SYNTAX-like score to quantify CAD. Such a program would find broad application in clinical care and might fulfill payer interests in pre-authorization for care

BRIEF SUMMARY

Embodiments include a method, system, and computer program product for associating coronary angiography image annotations with SYNTAX score for assessment of coronary artery disease. Aspects include receiving and processing a plurality of angiogram videos from a coronary angiography study into a plurality of frames for each of the plurality of angiogram videos, selecting and displaying a key frame from the plurality of frames for each of the plurality of angiogram videos in a browsing interface, and receiving a selection of one of the key frame from a user. Aspects further include displaying the angiogram video associated with the selected key frame in a video viewer interface, receiving a lesion annotation from the user for a frame of the angiogram video, and displaying a SYNTAX score questionnaire in the video viewer interface. Based on receiving answers to the SYNTAX score questionnaire from the user, aspect include annotating the frame of the angiogram video with the answers to the SYNTAX score questionnaire from the user and saving the answers to the SYNTAX score questionnaire with the annotated frame in a database.

Additional features and advantages are realized through the techniques of the present disclosure. Other embodiments and aspects of the disclosure are described in detail herein. For a better understanding of the disclosure with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The foregoing and other features, and advantages of the disclosure are apparent from the following detailed description taken in conjunction with the accompanying drawings in which:

DETAILED DESCRIPTION

Embodiments described herein are directed to methods, systems and computer program products for associating coronary angiography image annotations with SYNTAX scores for assessment of coronary artery disease. In exemplary embodiments, computation of a SYNTAX score is performed by viewing coronary angiograms, their lesion annotations, and the associated SYNTAX score questionnaire in a single user interface. In exemplary embodiments, the system allows the same coronary angiogram to be scored by multiple clinicians and facilitates the comparison of the computed scores, which can be used in conducting clinical trials.

In exemplary embodiments, SYNTAX score annotations are stored electronically and are associated with the underlying coronary angiogram imaging data. By storing the annotations and the imaging data electronically, the SYNTAX score annotations can be searched and aggregated, or retrieved for future inspection. Currently, there is no tool for allowing cardiologists to directly annotate lesions on the PACS data itself. Rather, cardiologists typically switch back and forth between browsing video runs of coronary angiogram imaging data in a PACS system and filling out a web-based SYNTAX score interview. Currently, the results of the web-based interview can only currently be saved as a PDF file, which do not include references to the coronary angiogram image data or schema for representing the answers to the interview questions.

Figure 1:
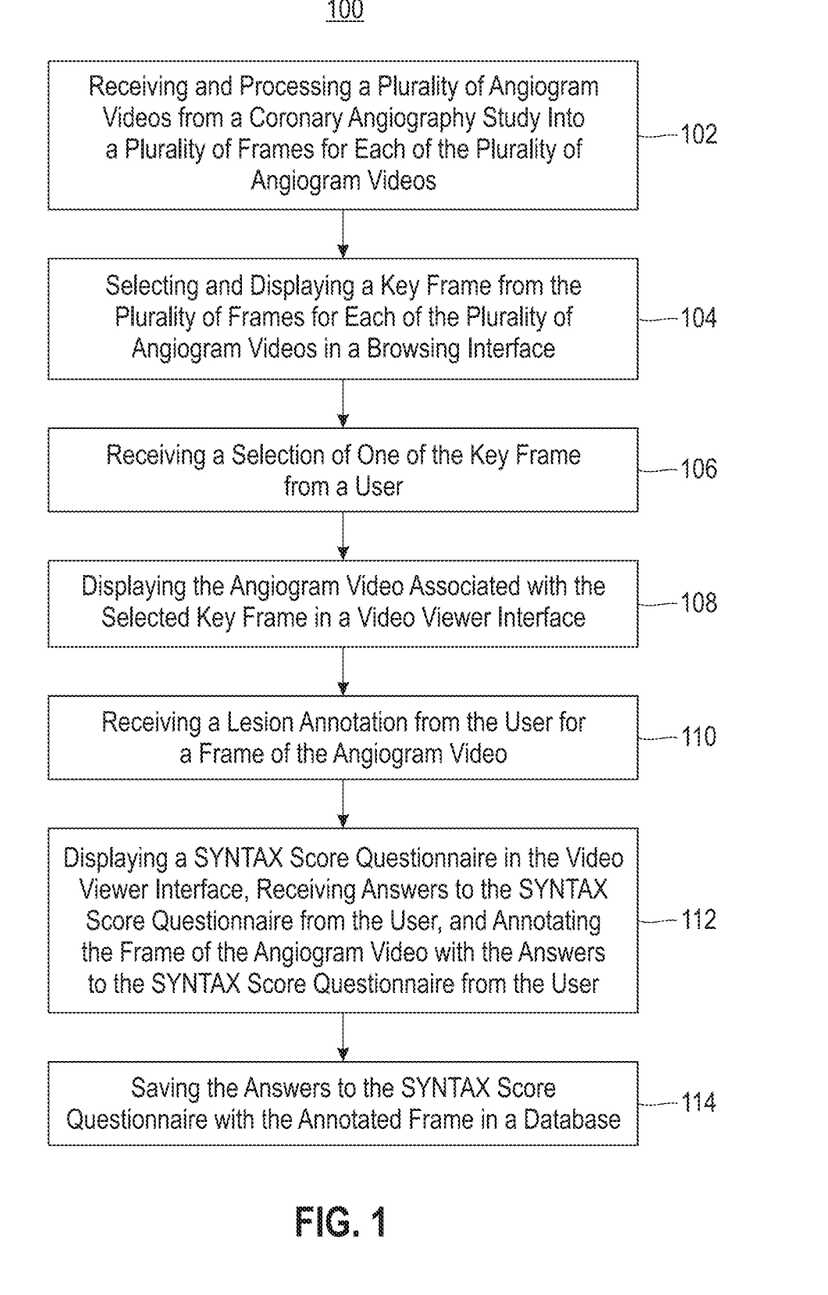
FIG. 1 depicts a process flow for associating coronary angiography image annotations with SYNTAX score for assessment of coronary artery disease in accordance with an embodiment.

Referring now to FIG. 1, a process flow of a method 100 for associating coronary angiography image annotations with SYNTAX scores for assessment of coronary artery disease in accordance with an embodiment is illustrated. As illustrated at block 102, the method 100 includes receiving and processing a plurality of angiogram videos from a coronary angiography study into constituent frames. Next, as shown at block 104, the method 100 includes selecting and displaying a key frame for each of the plurality of angiogram videos in a browsing interface. As shown at block 106, the method includes receiving a selection of a key frame from a user and responsively playing at least a portion of the angiogram video associated with the selected key frame in a video viewer interface. In exemplary embodiments, as the angiogram video is played, the user can freeze to a selected frame and start a lesion annotation. Next, as shown at block 108, the method includes displaying the angiogram video associated with the selected key frame in a video viewer interface. As shown at block 110, the method 100 also includes receiving a lesion annotation from a user for a frame of the angiogram video. In exemplary embodiments, the lesion annotation includes a location in the frame of the selected lesion and indicates if the lesion is a new lesion or an existing lesion. Based on receiving the lesion annotation, the method 100 includes displaying a SYNTAX score questionnaire in the video viewer interface and receiving answers to the SYNTAX score questionnaire from the user, as shown at block 112. Next, as shown at block 114, the method 100 includes saving the answers to the SYNTAX score questionnaire with the annotated frame in a database. The method 100 also includes computing and displaying a final SYNTAX score based on the answers to the SYNTAX score questionnaire for all identified lesions in the coronary angiography study. In exemplary embodiments, the method may also include generating a lesion report for a selected lesion that shows the answers of the SYNTAX score questionnaire for the selected lesion along with one or more frames illustrating the selected lesion.

In exemplary embodiments, once the lesions from a study are annotated the annotation information is saved in in the database. The annotation information includes metadata, such as the cardiologist login, the date and time of annotation, the number of lesions, a SYNTAX score for each lesion, and the total SYNTAX score. The annotation information also includes the lesion interview information for each identified lesion, which are the answers to the SYNTAX score questionnaire. The annotation information also includes lesion location information for each identified lesion. In exemplary embodiments, the lesion location information can include multiple frame locations in the run data, such as run 2, frame 12, (x, y)=(150, 160).

In exemplary embodiments, a coronary angiogram study is performed on a coronary artery of a patient which results in a collection of video sequences referred to as runs, where each of the runs illustrates a different point of view of the same coronary angiogram. In exemplary embodiments, the data from the coronary angiogram is stored electronically and includes a set of video sequence runs for the study, a key frame representing each run, a SYNTAX score questionnaire for each user annotating the runs, a list of video frames annotated within each run, a list of regions annotated per frame per run per annotator, and a SYNTAX score calculated per annotator.

Figure 2:
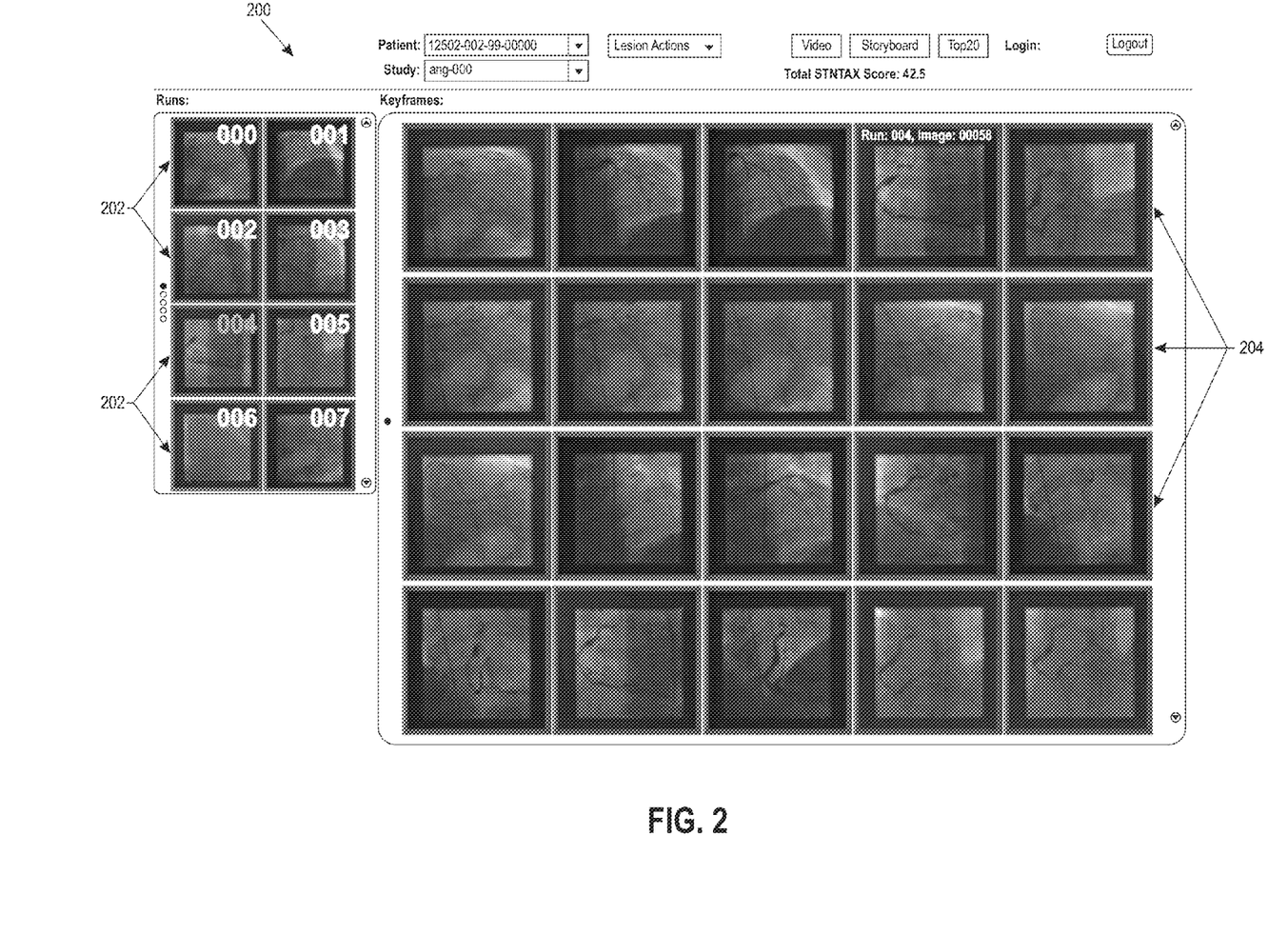
FIG. 2 depicts a browsing interface for a system for associating coronary angiography image annotations with SYNTAX score for assessment of coronary artery in accordance with an embodiment.

Calculating a SYNTAX score for a coronary angiogram study involves the scanning a large number of runs and frames for lesions. To assist with quick browsing of the coronary angiogram study, an imaging processing system can be used to perform a key frame extraction, which finds a representative sample of frames with contrast agent present. Since the contrast agent highlights the coronary arteries, a key frame detection algorithm can be used to identify frames with extended parallel curves. In one embodiment, these frames can be identified using estimated using edge detection, edge curve following, and pairing of curves on opposing sides of the artery. In exemplary embodiments, these frames are presented to the cardiologist in a browsing interface, as shown in FIG. 2. The browsing interface is configured to allow the user quick access to the most salient portions of the angiogram video the various runs.

In exemplary embodiments, to associate a coronary angiogram study with a SYNTAX score, the runs are loaded into a browsing interface 200 as shown in FIG. 2. The browsing interface 200 includes a plurality of runs that are each represented by a key frame 202. In one embodiment, the key frame 202 may be selected to be the first frame of a run, the middle frame of a run, the last frame of a run, or another frame of a run. When a user selects one of the runs by clicking on a key frame 202, a plurality of frames 204 from that run are displayed to the user. Once a user selects a frame 204, the run, or a portion of the run, associated with the frame 204 is loaded into a video viewer interface 300 as shown in FIG. 3.

Figure 3:
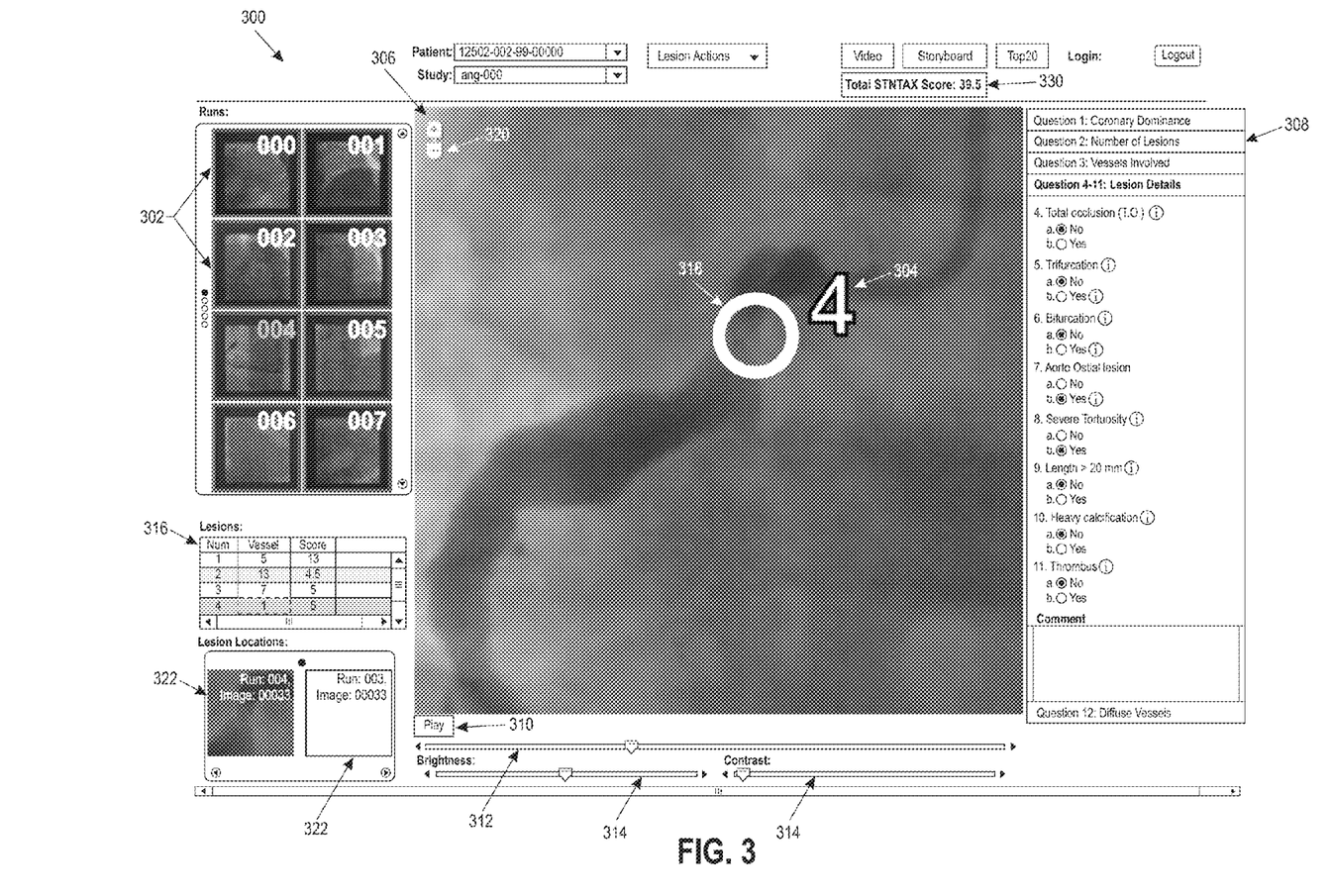
FIG. 3 depicts a video viewer interface for a system for associating coronary angiography image annotations with SYNTAX score for assessment of coronary artery in accordance with an embodiment.

Referring now to FIG. 3, video viewer interface 300 for associating coronary angiography image annotations with SYNTAX scores in accordance with an exemplary embodiment is shown. As illustrated, the video viewer interface 300 includes a plurality key frames 302 that each represents a run of a coronary angiogram study. The video viewer interface 300 also includes a video display portion 306 that is configured to playback video of a run, or a portion of a run associated with the selected key frame 302. In exemplary embodiments, the video viewer interface 300 includes a play/pause button 310, a progress bar 312, display controls 314, and zoom controls 320 that are configured to control the playback of the video. In exemplary embodiments, during playback of the video, a user can indicate a lesion 314 by clicking on a portion of the video. In one embodiment, once a user clicks on a lesion, a drop down menu may be displayed that allows the user to either associate the indicated lesion with an already know lesion listed in a lesion list 316 or to indicate a new lesion. Once the lesion has been given a label 304, the user can then complete a SYNTAX questionnaire 308 to score the lesion. In exemplary embodiments, the answers to the SYNTAX questionnaire 308 are saved along with the annotated image in the database. Once all of the lesions are annotated, a user can obtain a report that shows the answers of the SYNTAX questionnaire per lesion along with the lesion as shown in FIG. 4.

In exemplary embodiments, the video viewer interface 300 includes a list of lesions 316 that have been annotated for the coronary angiogram study. Each of the identified lesions in the list 316 includes vessel identification number and a score for each vessel. In exemplary embodiments, in response to a user selecting a lesion from the list of lesions 316, frames 322 that have been associated with the selected lesion are displayed in a portion of the video viewer interface 300. In addition, by selecting one of the frames 322, the video associated with the selected frame is loaded into the video display portion 306 of the video viewer interface 300. In exemplary embodiments, the video viewer interface 300 includes a total syntax score 330, which is automatically updated as the questionnaire 308 is completed for identified lesions.

Figure 4:
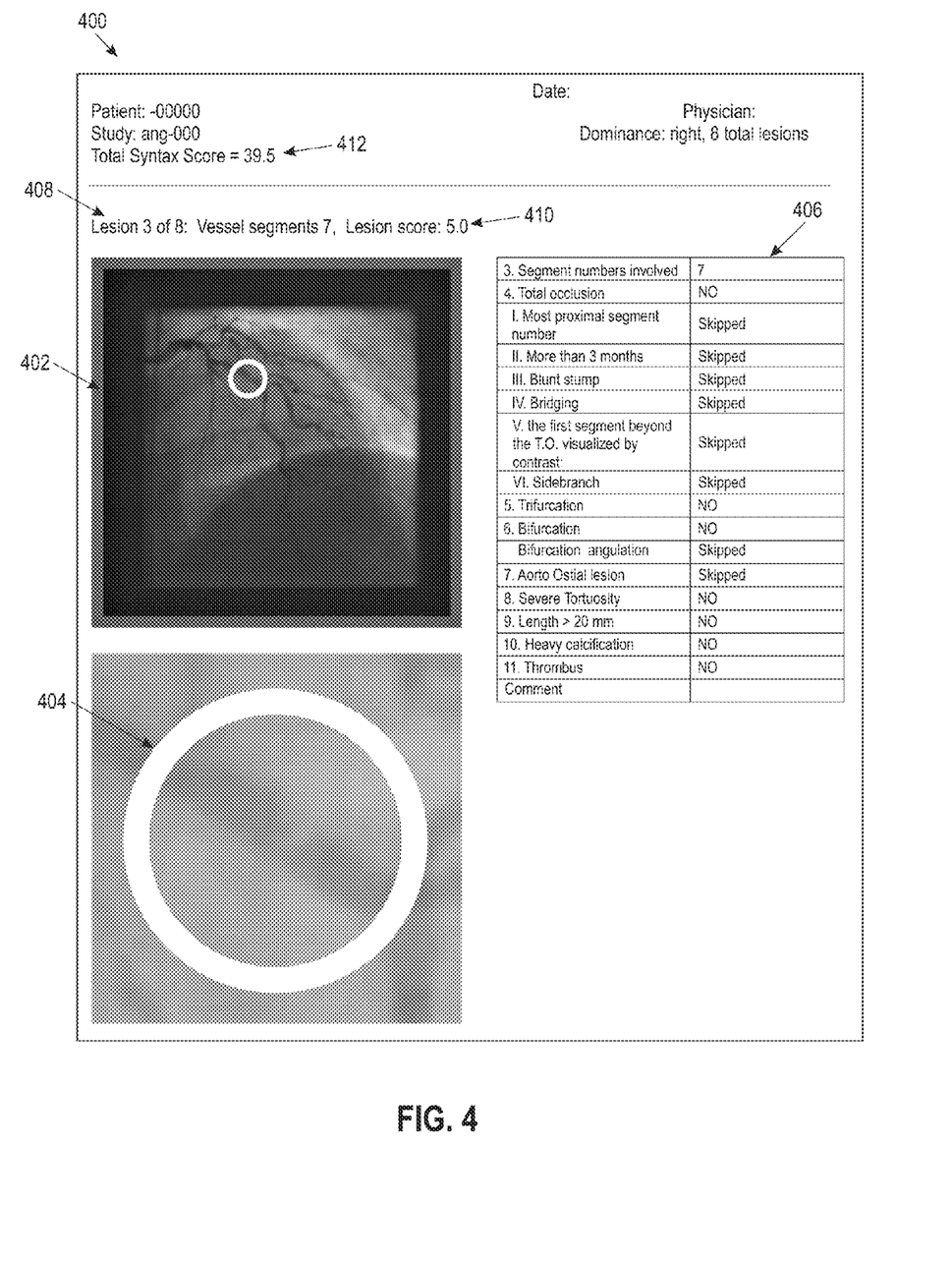
FIG. 4 depicts a lesion report generate by a system for associating coronary angiography image annotations with SYNTAX score for assessment of coronary artery in accordance with an embodiment.

Referring now to FIG. 4, a scoring report 400 in accordance with an exemplary embodiment is shown. In exemplary embodiments, the scoring report 400 can be generated using the system for associating coronary angiography image annotations with SYNTAX scores shown in FIG. 5. The scoring report 400 includes a frame 402 illustrating a selected lesion 408 from the coronary angiogram study and an expanded frame 404 that has been zoomed in to illustrate the selected lesion 408. The scoring report 400 also includes the answers of the SYNTAX score questionnaire 406 for the selected lesion 408. In exemplary embodiments, the scoring report 400 also includes a lesions score 410 for the selected lesion 408 and a total SYNTAX score 412 for the coronary angiogram study.

Figure 5:
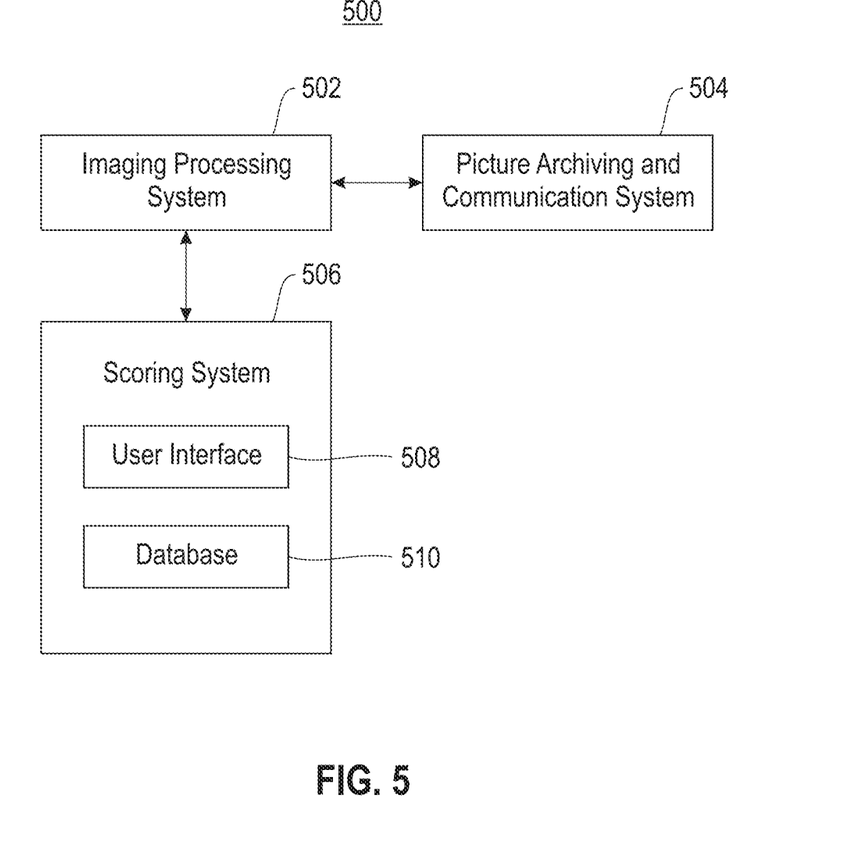
FIG. 5 depicts a block diagram of a system for associating coronary angiography image annotations with SYNTAX score for assessment of coronary artery disease in accordance with an embodiment.

Referring now to FIG. 5, a block diagram of a system 500 for associating coronary angiography image annotations with SYNTAX score in accordance with an exemplary embodiment is shown. As shown, the system 500 includes an imaging processing system 502 that receives and processes digital imaging and communications in medicine (DICOM) angiogram videos from a PACS system 504 into constituent frames. The DICOM angiogram videos include one or more runs that each are divided into a series of around 100-200 frames. This series of frames depicts a few cardiac cycles from the patient. In exemplary embodiments, the processing system 502 organizes the frames by patient, study, run, and frame number.

In exemplary embodiments, the system 500 also includes a scoring system 506, which includes a user interface 508 for associating coronary angiography image annotations with SYNTAX scores. In exemplary embodiments, the user interface 508 may include a browsing interface, as shown in FIG. 2, and video viewer interface, as shown in FIG. 3. The scoring system 506 also includes a database 510 that is configured to store the data associating the coronary angiography image annotations with the SYNTAX score. In exemplary embodiments, the data associating the coronary angiography image annotations with the SYNTAX score includes a patient identifier, a date of the study, a run identifier, a timestamp that identifies the specific frame from the identified run, and an (x, y) location in a specific frame of the lesion. In exemplary embodiments, each lesion may be associated with more than one frame from one or more runs. That is, the same lesion may be scored based on different viewpoints shown in different runs and in different frames of the same run. Although illustrated separately, the imaging processing system 502 and the scoring system 506 may be implemented on a single computing device, such as the computer illustrated in FIG. 6.

In exemplary embodiments, the scoring system 506 may be disposed on or be accessible by a webserver so that clinicians can access the scoring system 506 via the Internet. The scoring system 506 and the imaging processing system 502 can be configured to use user permissions to allow the coronary angiogram images and their annotations to be accessed by users with the proper permissions. In exemplary embodiments, the scoring system 506 can also compute summary statistics of any angiogram study across the physicians who have scored the study.

Figure 6:
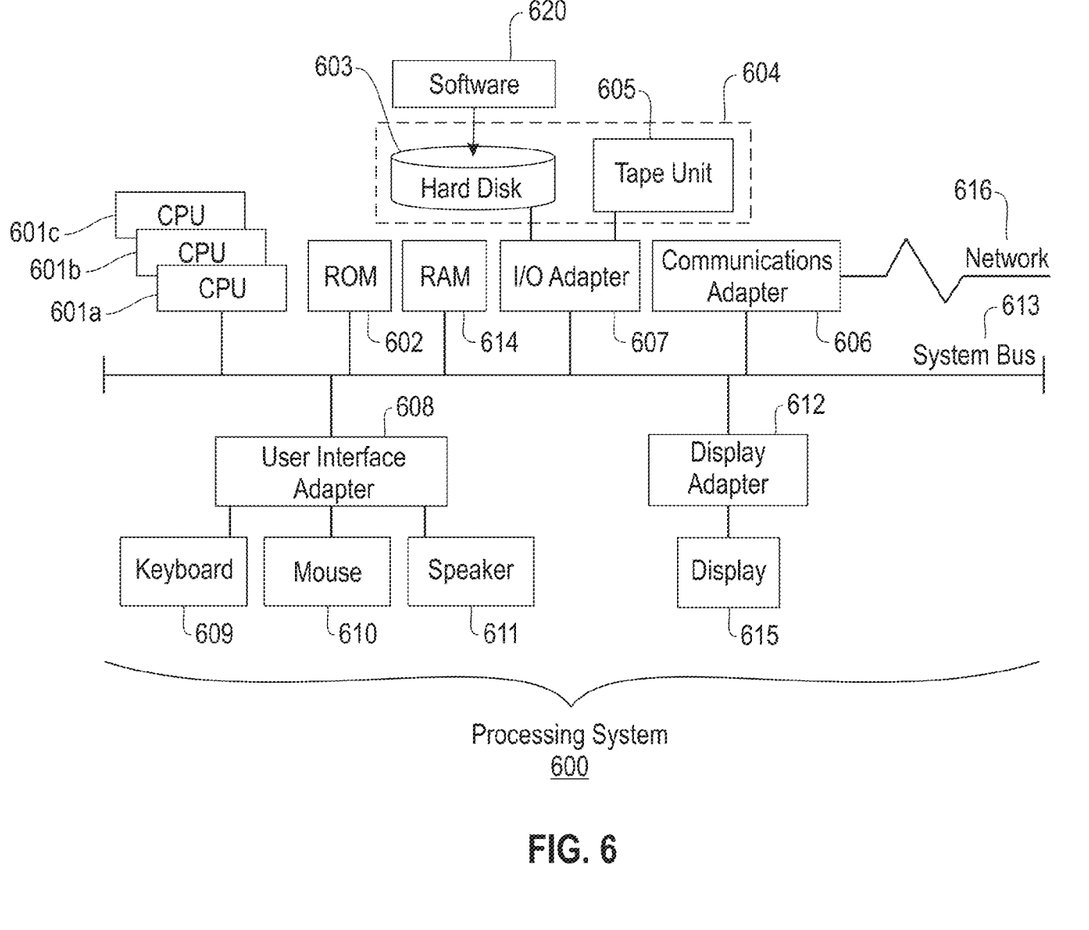
FIG. 6 depicts a processing system for practicing the teachings herein in accordance with an embodiment.

Referring to FIG. 6, there is shown an embodiment of a processing system 600 for implementing the teachings herein. In this embodiment, the system 600 has one or more central processing units (processors) 601a, 601b, 601c, etc. (collectively or generically referred to as processor(s) 601). In one embodiment, each processor 601 may include a reduced instruction set computer (RISC) microprocessor. Processors 601 are coupled to system memory 614 and various other components via a system bus 613. Read only memory (ROM) 602 is coupled to the system bus 613 and may include a basic input/output system (BIOS), which controls certain basic functions of system 600.

FIG. 6 further depicts an input/output (I/O) adapter 607 and a network adapter 606 coupled to the system bus 613. I/O adapter 607 may be a small computer system interface (SCSI) adapter that communicates with a hard disk 603 and/or tape storage drive 605 or any other similar component. I/O adapter 607, hard disk 603, and tape storage device 605 are collectively referred to herein as mass storage 604. Software 620 for execution on the processing system 600 may be stored in mass storage 604. A network adapter 606 interconnects bus 613 with an outside network 616 enabling data processing system 600 to communicate with other such systems. A screen (e.g., a display monitor) 615 is connected to system bus 613 by display adaptor 612, which may include a graphics adapter to improve the performance of graphics intensive applications and a video controller. In one embodiment, adapters 607, 606, and 612 may be connected to one or more I/O busses that are connected to system bus 613 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 613 via user interface adapter 608 and display adapter 612. A keyboard 609, mouse 660, and speaker 611 all interconnected to bus 613 via user interface adapter 608, which may include, for example, a Super I/O chip integrating multiple device adapters into a single integrated circuit.

Thus, as configured in FIG. 6, the system 600 includes processing capability in the form of processors 601, storage capability including system memory 614 and mass storage 604, input means such as keyboard 609 and mouse 160, and output capability including speaker 611 and display 615. In one embodiment, a portion of system memory 614 and mass storage 604 collectively store an operating system such as the AIX® operating system from IBM Corporation to coordinate the functions of the various components shown in FIG. 6.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiments were chosen and described in order to best explain the principles of the disclosure and the practical application, and to enable others of ordinary skill in the art to understand the disclosure for various embodiments with various modifications as are suited to the particular use contemplated.

Further, as will be appreciated by one skilled in the art, aspects of the present disclosure may be embodied as a system, method, or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present disclosure are described above with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed is:

1. A method for associating coronary angiography image annotations with a SYNTAX score for assessment of coronary artery disease comprising:
    receiving and processing, by a system comprising one or more processors, a plurality of angiogram videos from a coronary angiography study into a plurality of frames for each of the plurality of angiogram videos;
    extracting, by the system, a key frame from the plurality of frames for each of the plurality of angiogram videos, wherein extracting the key frame for each of the plurality of angiogram videos comprises detecting, by the system, a presence of a contrast agent in one or more frames of the plurality of frames of each given angiogram video, and using edge detection, edge curve following and pairing of curves on opposing sides of an artery to identify a representative frame of the given angiogram video having extended parallel curves;
    displaying to a user, by the system via a browsing interface, each of the extracted key frames;
    in response to receiving a selection from the user of a key frame from the displayed key frames, displaying, by the system via a video view interface, the angiogram video that is associated with the selected key frame;
    receiving, by the system, a lesion annotation from the user for a frame of the angiogram video;
    based on receiving the lesion annotation, displaying, by the system, a SYNTAX score questionnaire in the video viewer interface;
    based on receiving answers to the SYNTAX score questionnaire from the user, annotating, by the system, the frame of the angiogram video with the answers to the SYNTAX score questionnaire from the user;
    saving, by the system, the answers to the SYNTAX score questionnaire with the annotated frame in a database;
    computing and displaying a SYNTAX score for the lesion based on the answers to the SYNTAX score questionnaire; and
    generating a lesion report for a selected lesion that shows the answers of the SYNTAX score questionnaire for the selected lesion along with one or more frames illustrating the selected lesion.

2. The method of claim 1, wherein the plurality of angiogram videos from the coronary angiography study are received from a picture archiving and communication system.

3. The method of claim 1, further comprising computing and displaying a total SYNTAX score for the coronary angiography study based on the answers to the SYNTAX score questionnaire for all identified lesions in the coronary angiography study.

4. The method of claim 3, wherein the total SYNTAX score for the coronary angiography study is associated with the user who completed the SYNTAX score questionnaire.

5. The method of claim 4, further comprising sharing the total SYNTAX score for the coronary angiography study with one or more additional users for generating consensus opinions and performing a comparative evaluation of the coronary angiography study across users.

6. The method of claim 1, wherein annotating the frame of the angiogram video with the answers to the SYNTAX score questionnaire comprises recording a run identifier of the frame, a frame identifier of the frame, a position of the lesion in the frame, a patient identifier, and an identifier of the user who completed the SYNTAX score questionnaire.

7. A computer program product for associating coronary angiography image annotations with a SYNTAX score for assessment of coronary artery disease, the computer program product comprising a non-transitory computer readable storage medium having program code embodied therewith, the program code executable by a processor to:
    receive and process a plurality of angiogram videos from a coronary angiography study into a plurality of frames for each of the plurality of angiogram videos;
    extract a key frame from the plurality of frames for each of the plurality of angiogram video by at least detecting a presence of a contrast agent in one or more frames of the plurality of frames of each given angiogram video, and using edge detection, edge curve following and pairing of curves on opposing sides of an artery to identify a representative frame of the given angiogram video having extended parallel curves;
    display to a user, via a browser interface, each of the extracted key frames;
    in response to receiving a selection from a user of a key frame from the displayed key frames, display, via a video viewer interface, the angiogram video that is associated with the selected key frame;
    receive a lesion annotation from the user for a frame of the angiogram video;
    based on receiving the lesion annotation, display a SYNTAX score questionnaire in the video viewer interface;
    based on receiving answers to the SYNTAX score questionnaire from the user, annotate the frame of the angiogram video with the answers to the SYNTAX score questionnaire from the user;
    save the answers to the SYNTAX score questionnaire with the annotated frame in a database;
    compute and display a SYNTAX score for the lesion based on the answers to the SYNTAX score questionnaire; and generate a lesion report for a selected lesion that shows the answers of the SYNTAX score questionnaire for the selected lesion along with one or more frames illustrating the selected lesion.

8. The computer program product of claim 7, wherein the plurality of angiogram videos from the coronary angiography study are received from a picture archiving and communication system.

9. The computer program product of claim 7, further comprising computing and displaying a total SYNTAX score for the coronary angiography study based on the answers to the SYNTAX score questionnaire for all identified lesions in the coronary angiography study.

10. The computer program product of claim 9, wherein the total SYNTAX score for the coronary angiography study is associated with the user who completed the SYNTAX score questionnaire.

11. The computer program product of claim 7, wherein annotating the frame of the angiogram video with the answers to the SYNTAX score questionnaire comprises recording a run identifier of the frame, a frame identifier of the frame, a position of the lesion in the frame, a patient identifier, and an identifier of the user who completed the SYNTAX score questionnaire.

12. A system for associating coronary angiography image annotations with SYNTAX score for assessment of coronary artery disease comprising:
 a memory having computer readable computer instructions; and
 a processor for executing the computer readable instructions, the instructions including:
 receiving and processing, by the processor, a plurality of angiogram videos from a coronary angiography study into a plurality of frames for each of the plurality of angiogram videos;
 extracting, by the processor, a key frame from the plurality of frames for each of the plurality of angiogram videos, wherein extracting the key frame for each of the plurality of angiogram videos comprises detecting, by the processor, a presence of a contrast agent in one or more frames of the plurality of frames of each given angiogram video, and using edge detection, edge curve following and pairing of curves on opposing sides of an artery to identify a representative frame of the given angiogram video having extended parallel curves;
 displaying to a user, by the processor via a browsing interface, each of the extracted key frames;
 in response to receiving a selection from the user of a key frame from the displayed key frames, displaying, by the processor via a video view interface, the angiogram video that is associated with the selected key frame;
 receiving, by the system, a lesion annotation from the user for a frame of the angiogram video;
 based on receiving the lesion annotation, displaying, by the system, a SYNTAX score questionnaire in the video viewer interface;
 based on receiving answers to the SYNTAX score questionnaire from the user, annotating, by the system, the frame of the angiogram video with the answers to the SYNTAX score questionnaire from the user;
 saving, by the system, the answers to the SYNTAX score questionnaire with the annotated frame in a database;
 computing and displaying a SYNTAX score for the lesion based on the answers to the SYNTAX score questionnaire; and
 generating a lesion report for a selected lesion that shows the answers of the SYNTAX score questionnaire for the selected lesion along with one or more frames illustrating the selected lesion.

13. The system of claim 12, wherein the plurality of angiogram videos from the coronary angiography study are received from a picture archiving and communication system.

14. The system of claim 12, further comprising computing and displaying a total SYNTAX score for the coronary angiography study based on the answers to the SYNTAX score questionnaire for all identified lesions in the coronary angiography study.

* * * * *